US012636028B2

(12) United States Patent (10) Patent No.: US 12,636,028 B2

Connaughton et al. (45) Date of Patent: May 26, 2026

(54) MEDICAL SYSTEMS, DEVICES, AND RELATED METHODS THEREOF

(71) Applicant: Boston Scientific Scimed, Inc., Maple Grove, MN (US)

(72) Inventors: Enda Connaughton, County Galway (IE); Anthony O'Brien, Galway (IE); Aiden Flanagan, County Galway (IE); Charlene Deane, County Roscommon (IE); Michael Hughes, Claregalway (IE); Richard Crawford, Galway (IE); Martin Lawrence Fawdry, Galway (IE); Stephen McCooey, Dundalk (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 309 days.

(21) Appl. No.: 18/487,634

(22) Filed: Oct. 16, 2023

(65) Prior Publication Data

US 2024/0122615 A1 Apr. 18, 2024

Related U.S. Application Data

(60) Provisional application No. 63/379,927, filed on Oct. 18, 2022.

(51) Int. Cl.
*A61B 17/221* (2006.01)
*A61B 17/00* (2006.01)
(Continued)

(52) U.S. Cl.
CPC ...... *A61B 17/221* (2013.01); *A61B 17/00234* (2013.01); *A61B 17/0218* (2013.01);
(Continued)

(58) Field of Classification Search
CPC .......... A61B 2017/2215; A61B 17/221; A61B 2017/22079; A61B 17/22004;
(Continued)

(56) References Cited

U.S. PATENT DOCUMENTS

| | | | | |
|---|---|---|---|---|
| 6,083,257 A | * | 7/2000 | Taylor | B21F 45/00 623/1.46 |
| 6,099,534 A | * | 8/2000 | Bates | A61B 17/221 606/127 |

(Continued)

FOREIGN PATENT DOCUMENTS

WO        2018/094050 A2      5/2018

OTHER PUBLICATIONS

International Search Report and Written Opinion issued in International Application No. PCT/US2023/035219, issued Dec. 21, 2023 (9 pages).

*Primary Examiner* — Elizabeth Houston
*Assistant Examiner* — Daniel Icet
(74) *Attorney, Agent, or Firm* — Bookoff McAndrews, PLLC

(57) ABSTRACT

A method for removing one or more objects or materials from a body lumen includes delivering a tube and an expandable device to the body lumen to a position proximal to the one or more objects or materials. The expandable device is positioned with a lumen of the tube, and the expandable device includes a lumen extending from a distal portion to a proximal portion. The method further includes proximally retracting the tube such that the expandable device remains in the position proximal to the one or more objects or materials, distally advancing the expandable device such that the distal portion of the expandable device at least partially surrounds the one or more objects or materials, at least partially closing a distal end of the expandable device, and moving the expandable device (Continued)

proximally to remove the expandable device and the one or more objects or materials from the lumen.

20 Claims, 10 Drawing Sheets

(51) Int. Cl.
  *A61B 17/02* (2006.01)
  *A61B 17/22* (2006.01)

(52) U.S. Cl.
  CPC .. *A61B 17/22022* (2013.01); *A61B 17/22031* (2013.01); *A61B 2017/00238* (2013.01); *A61B 2017/00296* (2013.01); *A61B 2017/00336* (2013.01); *A61B 2017/00411* (2013.01); *A61B 2017/00818* (2013.01); *A61B 2017/00867* (2013.01); *A61B 2017/00982* (2013.01); *A61B 2017/22025* (2013.01); *A61B 2017/22034* (2013.01); *A61B 2017/22065* (2013.01); *A61B 2017/22074* (2013.01); *A61B 2017/2215* (2013.01); *A61B 2217/002* (2013.01)

(58) Field of Classification Search
  CPC  A61B 17/22–2258; A61B 2017/22051; A61B 1/00135
  See application file for complete search history.

(56)  References Cited

U.S. PATENT DOCUMENTS

| | | | | |
|---|---|---|---|---|
| 2001/0051810 A1* | 12/2001 | Dubrul | ................. | A61B 17/221 |
| | | | | 606/198 |
| 2002/0022859 A1* | 2/2002 | Hogendijk | .............. | A61F 2/013 |
| | | | | 606/200 |
| 2002/0068943 A1* | 6/2002 | Chu | ..................... | A61B 17/221 |
| | | | | 606/114 |
| 2006/0116693 A1 | 6/2006 | Weisenburgh et al. | | |
| 2008/0188866 A1 | 8/2008 | Karpiel et al. | | |
| 2011/0282353 A1* | 11/2011 | McHugo | .............. | A61B 1/3132 |
| | | | | 606/108 |
| 2013/0079797 A1 | 3/2013 | Diamant et al. | | |
| 2013/0131688 A1 | 5/2013 | Schwartz | | |
| 2014/0052146 A1 | 2/2014 | Curtis et al. | | |
| 2018/0235644 A1* | 8/2018 | Jaffe | ..................... | A61B 17/221 |
| 2018/0303499 A1* | 10/2018 | Bonneau | ................ | A61B 1/307 |
| 2024/0180618 A1* | 6/2024 | Riaz | ........................ | A61B 18/26 |

* cited by examiner

MEDICAL SYSTEMS, DEVICES, AND RELATED METHODS THEREOF

CROSS-REFERENCE TO RELATED APPLICATIONS

This application claims the benefit of priority of U.S. Provisional Patent Application No. 63/379,927, filed Oct. 18, 2022, the entirety of which is incorporated herein by reference.

TECHNICAL FIELD

This disclosure relates generally to medical systems, devices, and related methods. More specifically, at least certain embodiments of the disclosure relate to systems, devices, and related methods for endoscopic medical procedures, such as grasping, moving, extracting, and/or removing one or more objects or materials from body lumens, organs, or cavities, among other aspects.

BACKGROUND

Technological developments have given users of medical systems, devices, and methods the ability to conduct increasingly complex procedures on subjects. One challenge in the field of minimally invasive surgeries is associated with extracting objects or materials from within a subject, for example, such as extracting a biliary stone from the bile duct of a subject. Such procedures may require the use of multiple instruments to remove the biliary stone, such as, for example, a device to dilate the biliary duct, a device to trawl the bile duct, and a device to extract the biliary stone. Requiring the use of multiple instruments during the procedure may lead to various procedural issues, an increase in the time of the procedure, and/or an increased risk of injury to the subject. As such, there is a need for systems, devices, and methods that address one or more of these difficulties or other related problems.

SUMMARY

Examples of the disclosure relate to, among other things, systems, devices, and methods for performing one or more medical procedures with the medical systems and devices. Each of the examples disclosed herein may include one or more of the features described in connection with any of the other disclosed examples.

According to one method for removing one or more objects or materials from a body lumen, the method comprises: delivering a tube and an expandable device to the body lumen to a position proximal to the one or more objects or materials, wherein the expandable device is positioned with a lumen of the tube, and wherein the expandable device includes a lumen extending from a distal portion to a proximal portion; proximally retracting the tube such that the expandable device remains in the position proximal to the one or more objects or materials; distally advancing the expandable device such that the distal portion of the expandable device at least partially surrounds the one or more objects or materials; at least partially closing a distal end of the expandable device; and moving the expandable device proximally to remove the expandable device and the one or more objects or materials from the lumen.

Any of the examples described herein may have any of the following features in any combination. The method may further comprise, before distally advancing the expandable device, expanding the distal portion of the expandable device with a balloon. At least the distal portion of the expandable device may be formed of a shape-memory material that expands on its own when no longer positioned within the lumen of the tube. At least partially closing the distal end of the expandable device may include proximally retracting one or more pull lines coupled to the distal end of the expandable device. Proximally retracting the one or more pull lines may cause the distal end of the expandable device to taper radially inward to at least partially close the distal end of the expandable device.

The method may further comprise delivering a medical device or a scope through the lumen of the tube and through the lumen of the expandable device, wherein the medical device or the scope includes one or more visualization devices. Distally advancing the expandable device may include abutting a distal end of the scope with one or more radially inward extensions on an inner surface of the expandable device, and distally advancing the scope to distally advance the expandable device.

The method may further comprise, after at least partially closing the distal end of the expandable device, delivering an energy delivery device through the lumen of the tube and the lumen of the expandable device; and activating the energy delivery device one or more times to direct energy toward the one or more objects or materials. In some embodiments, the tube and the expandable device may be delivered to the body lumen via an incision.

The method may further comprise depositing the one or more objects or materials into a mesh basket positioned proximal to the lumen. Depositing the one or more objects or materials into the mesh basket may include delivering fluid through the lumen of the tube and into the expandable device. In some embodiments, the lumen may be a biliary duct, and the one or more objects or materials may include one or more biliary stones.

In an additional or alternative method for removing one or more biliary stones from a bile duct, the method may comprise: making an incision in a subject adjacent to the bile duct; delivering a tube and an expandable device, via the incision, to the bile duct to a position proximal to the one or more biliary stones, wherein the expandable device is positioned with a lumen of the tube, and wherein the expandable device includes a lumen extending from a distal portion to a proximal portion; proximally retracting the tube such that the expandable device remains in the position proximal to the one or more biliary stones; distally advancing the expandable device such that the distal portion of the expandable device at least partially surrounds the one or more biliary stones; at least partially closing a distal end of the expandable device; and moving the expandable device proximally to remove the expandable device and the one or more biliary stones or materials from the bile duct.

The method may further comprise, before distally advancing the expandable device, expanding the distal portion of the expandable device and dilating a portion of the bile duct by expanding a balloon positioned within a distal portion of the lumen of the expandable device. In some embodiments, at least partially closing the distal end of the expandable device includes proximally retracting one or more pull lines coupled to the distal end of the expandable device, and wherein proximally retracting the one or more pull lines causes the distal end of the expandable device to taper radially inward to at least partially close the distal end of the expandable device.

The method may further comprise delivering a medical device or a scope through the lumen of the tube and through the lumen of the expandable device, wherein the medical device or the scope includes one or more visualization devices, and wherein distally advancing the expandable device includes abutting a distal end of the scope with one or more radially inward extensions on an inner surface of the expandable device, and distally advancing the scope to distally advance the expandable device. The method may further comprise after at least partially closing the distal end of the expandable device and before moving the expandable device proximally, delivering an energy delivery device through the lumen of the tube and the lumen of the expandable device; and activating the energy delivery device one or more times to direct energy toward the one or more biliary stones to fragment or break up the one or more biliary stones. The method may further comprise depositing the one or more fragmented or broken up biliary stones into a mesh basket positioned proximal to the lumen.

In an alternative embodiment, a medical system may include a tube having a lumen and an expandable device having a proximal portion, a distal portion, and an intermediate portion between the proximal portion and the distal portion. The expandable device may include a lumen extending from the proximal portion to the distal portion. In a first configuration, the expandable device may be positioned with the lumen of the tube, may be in an unexpanded state, and a distal end of the distal portion may be open. In a second configuration, the expandable device may be at least partially extended from the lumen of the tube, may be in an expanded state, the distal end of the distal portion may be open and larger than the distal end in the first configuration. In a third configuration, the expandable device may be at least partially extended from the lumen of the tube, may be in the expanded state, and the distal end of the distal portion may be at least partially closed. In the third configuration, the expandable device may be configured to be retracted proximally and retain one or more objects or materials within the expandable device. The medical system may further comprise a scope configured to be delivered through the lumen of the tube and at least partially through the lumen of the expandable device. The scope may include one or more visualization devices. An energy delivery device may be configured to be delivered through the lumen of the tube and at least partially through the lumen of the expandable device. The energy delivery device may be configured to at least partially break up or fragment the one or more objects or materials.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1A:
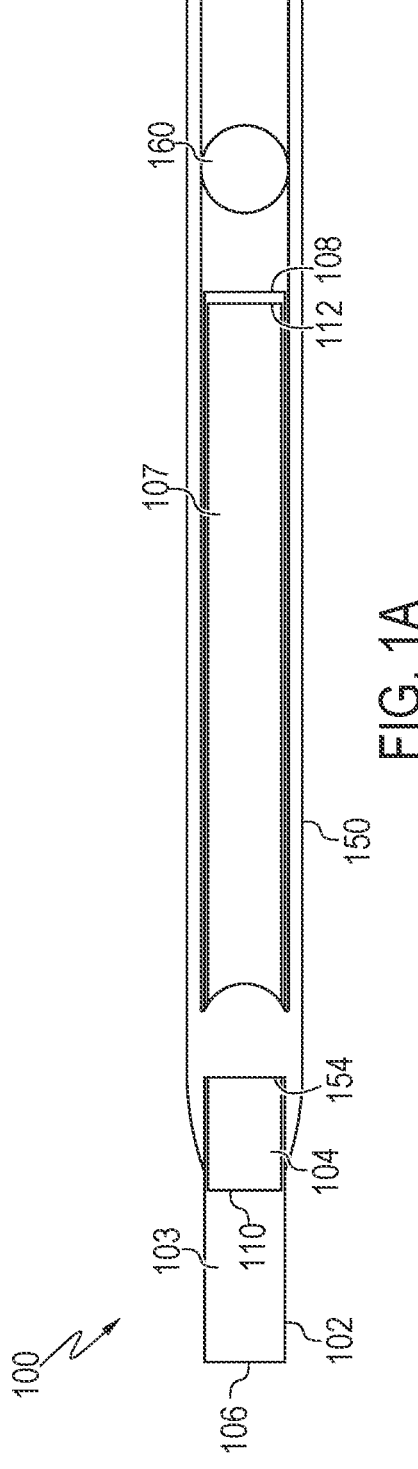
FIGS. 1A-1E are side cross-sectional views of an exemplary medical system/device at least partially within a body lumen at various points or steps of an exemplary procedure, according to aspects of this disclosure.

Reference will now be made in detail to aspects of this disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., a patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Embodiments of the disclosure may solve one or more of the limitations in the art. The scope of the disclosure, however, is defined by the attached claims and not the ability to solve a specific problem. The disclosure, in certain embodiments, is drawn to inserting a medical device into a body lumen, such as a duct. The duct may include, for example, the common bile duct, cystic duct, hepatic duct, among others.

FIGS. 1A-1E show side cross-sectional views of an exemplary medical system 100 at various points, stages, or steps during an exemplary procedure in accordance with an embodiment of this disclosure. As discussed in detail below, medical system 100 includes a primary device or an outer tube 102 (hereinafter "tube" 102) and a secondary device or expandable device 104 (hereinafter device 104). Furthermore, tube 102 and/or device 104 may be at least partially movable relative to the other, for example, to help enclose and/or remove one or more objects or materials from a lumen 150 of a subject. For example, tube 102 may be movable relative to device 104, and/or vice versa. Additionally, FIG. 2 illustrates an exemplary method or process 200 that one or more users may perform with any of the medical systems, devices, or portions of systems discussed herein, for example, medical system 100.

Figure 2:
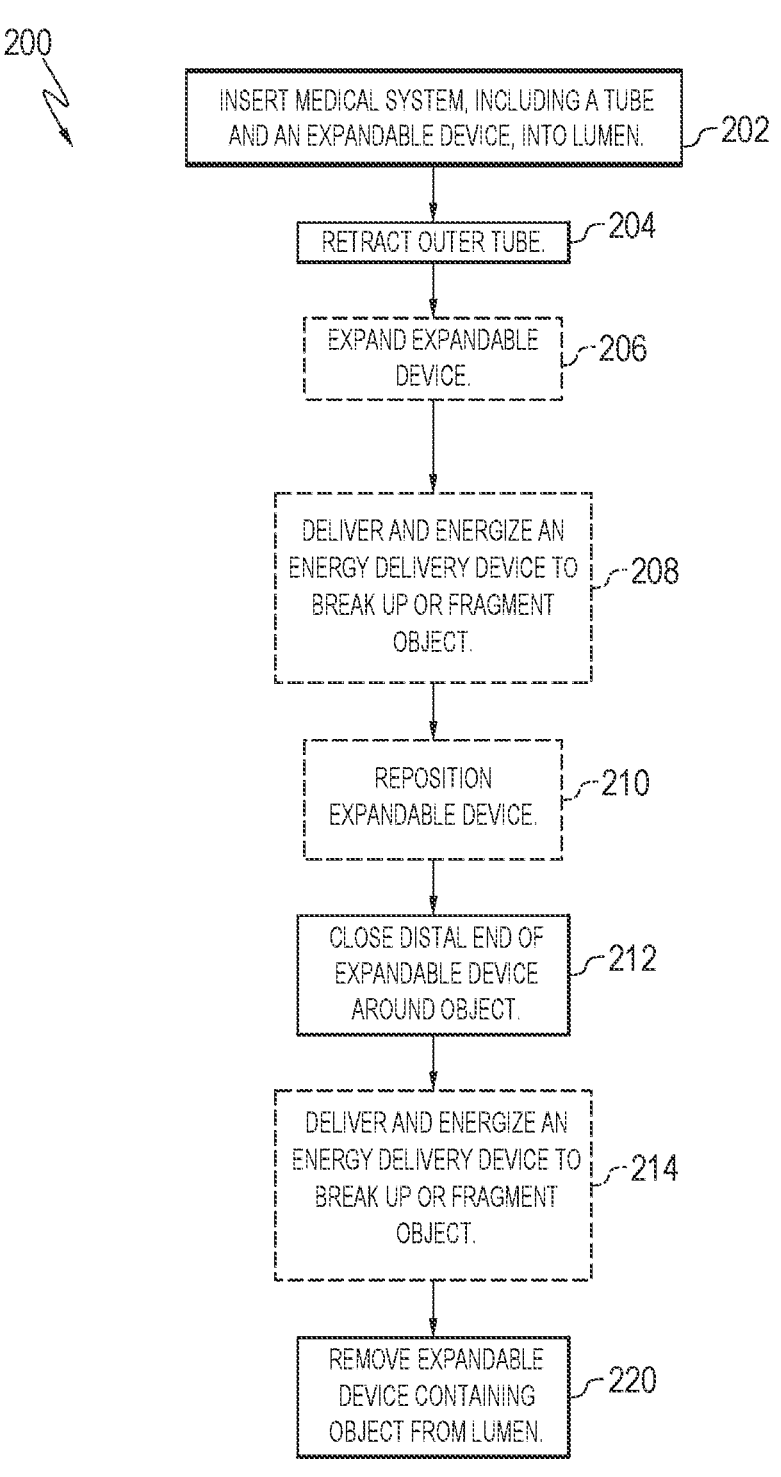
FIG. 2 is a flow diagram of an exemplary method, according to aspects of this disclosure.

Specifically, FIG. 1A depicts medical system 100 during insertion into a lumen 150 of a subject. As shown in FIG. 1A, tube 102 may be at least partially cylindrical. Tube 102 may be formed of a rigid or a semi-rigid material (e.g. polypropylene plastic, high-density polyethylene plastic, Nitinol, stainless steel, elgiloy (e.g., a non-magnetic Cobalt- Chromium-Nickel-Molybdenum alloy), nylon (Grilamid®, Crystamid e), Pebax®, etc.) and, in at least some embodiments, is straight without bends. Although not shown, it should be appreciated that in some embodiments, tube 102 may include one or more bends or curvatures along a longitudinal length between a proximal end 106 and a distal end 108. For example, one or more portions of tube 102 may be S-shaped or U-shaped. Additionally or alternatively, one or more surfaces or portions of tube 102 may be at least partially coated with any biocompatible material commonly known in the art (i.e., silicone-based lubricants, coatings, gels, fluids, anticoagulants (heparin), polytetrafluoroethylene (PTFE), etc.). For example, coating one or more outer surfaces or portions of tube 102 may facilitate the insertion, positioning, and/or removal of medical system 100 into/out of lumen 150. Additionally or alternatively, tube 102 may further comprise a pull line (not shown) extending proximally from a proximal end of tube 102. For example, the pull line (not shown) may be used to facilitate the insertion, positioning, and/or removal of tube 102 and/or medical system 100 into and/or out of lumen 150. Additionally or alternatively, coating one or more inner surfaces or portions of tube 102 may facilitate the insertion, positioning, and/or removal of device 104 through a lumen 103 of tube 102, to be described further herein.

A longitudinal length of tube 102 may range from approximately 10 centimeters to approximately 30 centimeters, for example, approximately 20 centimeters. However, it is understood that tube 102 may include various other shapes, sizes, and/or lengths than those shown and described herein. For example, tube 102 may be inserted into a subject via an opening 154, such as an incision through tissue in the subject. Accordingly, tube 102 may be sufficiently sized such that at least a proximal end 106 of tube 102 remains outside of the subject, and at least a distal end 108 of tube 102 is within lumen 150.

As mentioned above, tube 102 further comprises lumen 103 extending from proximal end 106 to distal end 108 of tube 102. Lumen 103 may be sufficiently sized to receive secondary device (e.g., a stent) 104, to be described in further detail below. By way of example only, in some embodiments, tube 102 of medical system 100 may include an outer diameter of approximately 4 millimeters to approximately 10 millimeters, and lumen 103 may include an inner diameter of approximately 3 millimeters to approximately 9 millimeters. Accordingly, a wall thickness of tube 102 may range from approximately 0.5 millimeters to approximately 3.5 millimeters. Outer diameter and/or inner diameter of tube 102 may be consistent along an entire longitudinal length of tube 102. In alternative examples (not shown), the outer and/or inner diameters of tube 102 may vary along the longitudinal length. For example, the outer and/or inner diameter of tube 102 may decrease along the longitudinal length such that the inner and/or outer diameter is greater on a proximal portion of tube 102 as compared to a distal portion of tube 102. In alternative examples (not shown), the wall thickness of tube 102 may vary along the longitudinal length. For example, the wall thickness of tube 102 may be greater on a proximal portion of tube 102 as compared to a distal portion of tube 102, or vice versa. An increased wall thickness on one or more portions of tube 102 may help provide for additional stability during the procedure. In some aspects, tube 102 may have a lateral cross-sectional shape, such as, for example, an oval, circle, square, rectangle, star, or any shape commonly known in the art.

An external surface of tube 102 may further comprise one or more various features (not shown), for example, indentations, raised surfaces, markings (e.g., radiopaque markings), etc., or any combination thereof. These features may serve a variety of purposes. For example, the indentations and/or raised surfaces may help tube 102 to remain in place during a procedure, for example, by way of increasing the surface area of the external surface of tube 102. Additionally or alternatively, one or more markings may provide visual cues or indicators for a user to ensure medical system 100 is appropriately placed within lumen 150, for example, when using one or more visualization devices, fluoroscopy, etc.

Medical system 100 further comprises secondary or expandable device 104. Device 104 may comprise any device having expandable and/or memory-shape (or shape-memory) characteristics, such as, for example, a stent. Devices comprising memory-shape materials may be configured to "remember" an original or specific shape and return to that same shape, for example, when subject to external stimuli (e.g., mechanical forces or temperature changes) and/or after a stimuli or constraint is removed. Accordingly, device 104 may be formed of one or more flexible or semi-flexible materials, such as, for example, plastic, Nitinol, stainless steel, elgiloy (e.g., a non-magnetic Cobalt-Chromium-Nickel-Molybdenum alloy), shape-memory polymers, or any material commonly known in the art. In a first configuration, device 104 may be positioned within lumen 103 in an unexpanded state such that a distal end 112 of device 104 is proximal to distal end 108 of tube 102. A proximal end 110 of device 104 may be distal to proximal end 106 of tube 102. This arrangement of device 104 is such that device 104 may be delivered or positioned within lumen 150.

In alternative configurations, proximal end 110 of device 104 may be aligned with or extend proximally beyond proximal end 106 of tube 102. Accordingly, a longitudinal length of device 104 may range from approximately 5 centimeters to approximately 30 centimeters. Similarly, an outer diameter of device 104 may range from approximately 2 millimeters to approximately 15 millimeters in the first, unexpanded configuration. In the first, unexpanded configuration, device 104 may be at least partially cylindrical. However, it is noted that device 104 may include various other shapes, sizes, and/or lengths than those shown and described herein. For example, device 104 may have a lateral cross-sectional shape that is an oval, circle, square, rectangle, star, or any shape commonly known in the art.

Furthermore, device 104 may comprise one or more characteristics similar to those described above with respect to tube 102. For example, an outer surface of device 104 may further comprise various features (not shown). These features may include, for example, indentations, raised surfaces, markings, etc., or any combination thereof. Additionally, device 104 need not be the same shape as tube 102. For example, device 104 may include a circular cross-section, and tube 102 may an ovular or square cross-section, or vice versa. Alternative combinations are also possible.

Device 104 comprises a lumen 107 extending from proximal end 110 to distal end 112. Similar to tube 102, one or more surfaces of device 104 may be at least partially coated with any material commonly known in the art to facilitate the insertion, positioning, and/or removal of device 104 through a lumen 103 of tube 102 or the insertion, positioning, and/or removal of an additional device (not shown) through lumen 107 of device 104. Additionally or alternatively, one or more surfaces of device 104 may be at least partially coated to facilitate the insertion, positioning, and/or removal of device 104 through lumen 150. The walls (e.g., interior walls) forming lumen 107 of device 104 may additionally or alternatively be insulated, coated, or otherwise formed to help prevent damage to surrounding tissue in or around lumen 150 when performing certain procedures such as, for example, lithotripsy. Additionally or alternatively, the walls forming lumen 107 may be at least partially porous and/or may comprise a plurality of cavities facilitating the absorption of shock waves through elastic deformation. In some aspects, the material comprising the walls forming lumen 107 may be elastic, for example, formed of silicone.

Referring to FIGS. 1A and 2, in a step 202, medical system 100 may be inserted into lumen 150, for example, via opening 154. Opening 154 may be, for example, an incision or a natural orifice of the subject. In some examples, step 202 may include making an incision, for example, to access lumen 150. The incision may be adjacent to the bile duct and/or the target site. Lumen 150 may contain, for example, one or more objects and/or materials 160 (hereinafter "object" 160). In some aspects, object 160 may be a stone, for example, a biliary stone. Medical system 100 may be inserted into lumen 150 via opening 154 and positioned such that distal end 108 of tube 102 is proximal or adjacent to object 160. Although not shown, it is noted that medical system 100 may also be inserted into lumen 150 through a trocar, sheath, cannula, or any other device commonly used in the art to create and/or maintain opening 154. Additionally, as previously described, at least a portion of proximal end 106 of tube 102 may remain outside of, or extend proximally from, opening 154. In some embodiments, medical system 100 may be delivered to the target site by means of a delivery device (not shown), such as, for example, a scope. Once medical system 100 is in place, the delivery device (not shown) may be removed.

Figure 1B:
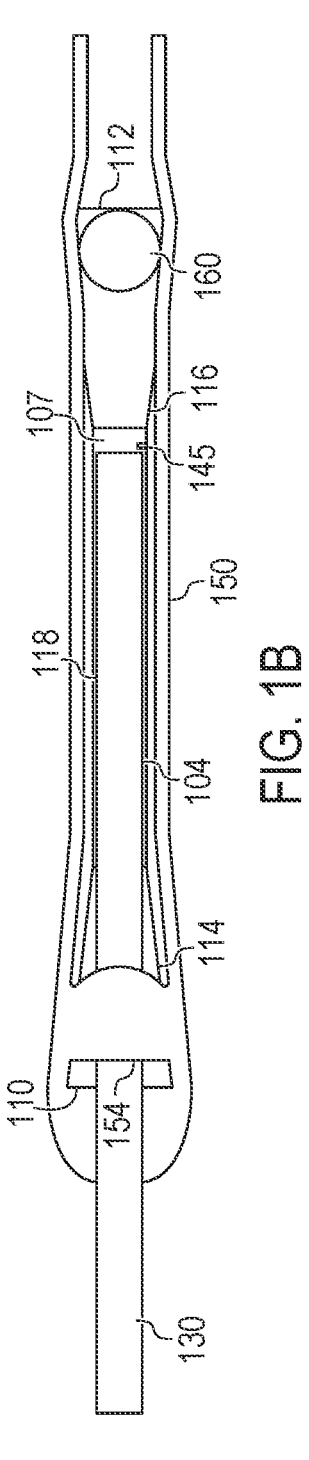

Once medical system 100 is in the desired position, step 204 may include removing or at least partially retracting tube 102 from lumen 150, and leaving device 104 within lumen 150, as shown in FIG. 1B. Tube 102 may be retracted or removed by grasping proximal end 106 and pulling proximal end 106 proximally. In some embodiments, prior to the removal of tube 102, a scope 130 (to be described in further detail below) may be inserted through lumen 103 of tube 102 and lumen 107 of device 104. An internal surface of device 104 may include one or more features 145 extending radially inward. For example, the one or more feature(s) 145 may include one or more bumps, ledges, lips, hooks, or any other features commonly known in the art that may extend partially or entirely around the internal surface of device 104 (e.g., extending radially inward). In this aspect, a distal end of scope 130 (e.g., a distal end face and/or an outer circumference of scope 130) may be used to push against, or abut, the one or more feature(s) 145 to assist in maintaining the position of device 104 while tube 102 is retracted.

Upon removal of tube 102, a proximal portion 114 (e.g., a cross-sectional area of proximal portion 114) of device 104 and a distal portion 116 (e.g., a cross-sectional area of distal portion 116) of device 104 may each expand (e.g., radially outward). For example, due to the shape-memory characteristics/materials of device 104, as previously described, device 104 may expand on its own as device 104 is released/removed from lumen 103 of tube 102 and/or once device 104 is no longer positioned within lumen 103 of tube 102. Device 104 may expand such that one or more external surface(s) of device 104 touch, abut, or press against, one or more internal surfaces of lumen 150. An intermediate portion 118 (e.g., a cross-sectional area of intermediate portion 118) may remain unchanged or may similarly expand, as well.

In alternative configurations, tube 102 may be inserted into lumen 150 without device 104 preloaded within lumen 103. In such a configuration, device 104 may be loaded or inserted into lumen 103 of tube 102, for example, once tube 102 is in a desired position within lumen 150. Thus, once device 104 is in position within lumen 103, tube 102 may be retracted and/or removed, as previously described.

Before, during, or after the removal of tube 102, scope 130 may be inserted through lumen 107 of device 104. Scope 130 may include one or more visualization devices (e.g., cameras), one or more illumination devices (e.g., light sources), and/or one or more lumens (not shown) to assist with visualization and/or delivering, positioning, and/or removing accessory medical devices during a procedure.

Still referring to FIG. 1B, proximal portion 114 and/or distal portion 116 may expand by nature of the memory-shape, or shape-memory, material comprising device 104. For example, proximal portion 114 and/or distal portion 116 may be naturally biased to an expanded configuration. In some configurations, however, method 200 may include an optional step 206, in which proximal portion 114 and/or distal portion 116 may be expanded manually by means of, for example, a balloon inserted radially within one or more portions of device 104. In the expanded configuration, external walls of proximal portion 114, intermediate portion 118, and/or distal portion 116 may press against opening 154 and/or internal walls of lumen 150, respectively. The radially-outward forces applied by the external walls of proximal portion 114 and distal portion 116 against the respective tissue may assist in securing device 104 in position within opening 154 and/or lumen 150. The radially-outward forces of proximal portion 114 may assist in further opening or maintaining opening 154. The radially-outward forces of distal portion 116 may also assist in expanding lumen 150 to further facilitate the capturing and/or removal of object 160, to be described in further detail below.

With tube 102 removed, proximal portion 114, intermediate portion 118, and distal portion 116 may have circular cross-sections. Proximal portion 114, intermediate portion 118, and/or distal portion 116 may assist in widening or dilating opening 154 and/or lumen 150. Proximal portion 114 and distal portion 116 may be variably shaped. For example, the internal and/or external walls of proximal portion 114 and/or distal portion 116 may taper in size (e.g., radially) towards intermediate portion 118. The internal and/or external walls of proximal portion 114 and/or distal portion 116 may be alternatively shaped to provide additional stability within lumen 150 upon deployment of device 104. Additionally or alternatively, proximal portion 114 and distal portion 116 may vary in size and shape relative to one another. For example, proximal portion 114 may be longer (e.g., longitudinally) than distal portion 116, or vice versa. Proximal portion 114 may, additionally or alternatively, include a greater and/or steeper taper, as compared to distal portion 116, or vice versa.

In some embodiments, proximal portion 114, distal portion 116, and/or intermediate portion 118 may be formed of the same material. Alternatively, one or more proximal portion 114, distal portion 116, and/or intermediate portion 118 may be formed of different materials having different characteristics or of the same material having different characteristics. For example, if device 104 is comprised of woven Nitinol threads or wires, such as a stent, the threads or wires forming proximal portion 114 may differ in size and/or pitch in comparison to threads or wires forming distal portion 116 and/or intermediate portion 118. Many other combinations are also possible.

Once device 104 is deployed (e.g., by removing tube 102), the longitudinal length of device 104 may decrease overall. This may be a result of the expansion of one or more proximal portion 114, distal portion 116, and/or intermediate portion 118. For example, as the outer diameter of one or more proximal portion 114, intermediate portion 118, and/or distal portion 116 increases, the length of the same one or more proximal portion 114, intermediate portion 118, and/or distal portion 116 may decrease. Accordingly, the overall length of device 104 may decrease upon deployment of device 104. Thus, the longitudinal length of device 104 in an expanded, deployed configuration may range from approximately 3 centimeters to approximately 29 centimeters, for example, approximately 5 centimeters to approximately 20 centimeters, for example, approximately 10 centimeters. In the deployed state, the outer diameter of at least a portion of proximal portion 114, intermediate portion 118, and distal portion 116 may range from approximately 2.5 millimeters to approximately 30 millimeters, for example, approximately 5 millimeters to approximately 25 millimeters, for example, approximately 15 millimeters.

The radial expansion of distal portion 116 may result in the radial expansion of lumen 150, which may help to allow for device 104 to surround object 160. For example, the radial expansion may help to form opening(s) between object 160 and the internal walls of lumen 150, and then device 104 may pass through the formed openings to help at least partially surround object 160.

To assist with positioning object 160 within device 104, additional devices may be used. For example, in some embodiments, a device having a screw, a piercing component, and/or a suction element could be used to attach to a proximal side of object 160 to pull or reposition object 160 into lumen 107 of device 104. Additionally or alternatively, a trawling device may be passed around object 160 and opened or deployed distally of object 160. The trawling mechanism may include, for example, a cage, a net, a stent, a balloon, or any combination thereof. Once the trawling mechanism is opened or deployed, the trawling mechanism may be proximally retracted such that the trawling mechanism pulls object 160 towards or into lumen 107 of device 104. Additionally or alternatively, a device having an array of rods, prongs, and/or splines may be passed around object 160 and opened or deployed distally of object 160. The device may further comprise a suture that may be tightened around object 160. Once the suture is tightened around object 160, the device may be pulled or otherwise urged proximally, thereby pulling object 160 into lumen 107 of device 104. Additionally or alternatively, a device comprising a spiral or coil may be used to reposition object 160. For example, the spiral or coil may be rotated around object 160. Continued rotation would draw object 160 proximally, similar to a corkscrew action.

Figures 4, 5:
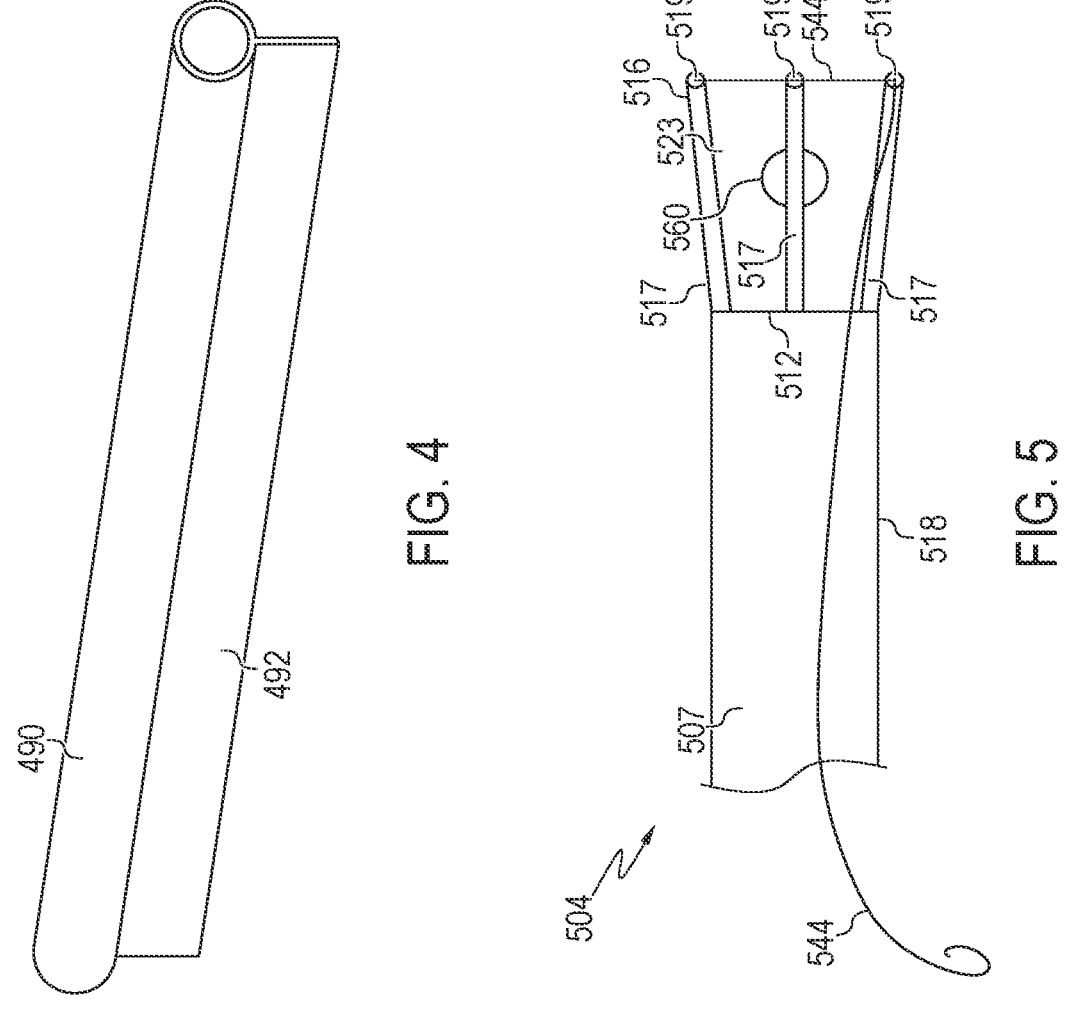
FIG. 4 is a perspective view of a section of an alternative exemplary medical device, according to aspects of this disclosure.
FIG. 5 is a side view of an alternative exemplary medical device, according to aspects of this disclosure.

In alternative embodiments, the spiral or coil may further comprise a rib 492 extending radially outwards from a wire 490 forming the spiral or coil, as shown in FIG. 4. Rib 492 may assist, for example, in maintaining object 160 (shown in FIGS. 1A-C) and/or object fragments 160' (shown in FIGS. 1D-1E) within the spiral or coil. Rib 492 may be formed of one or more flexible or semi-flexible materials, such as, for example, polypropylene plastic, high-density polyethylene plastic, Nitinol, stainless steel, elgiloy (e.g., a non-magnetic Cobalt-Chromium-Nickel-Molybdenum alloy), silicone, or any material commonly known in the art.

Rib 492 may extend from wire 490 so as to reduce or close a gap or spacing between each of the spirals or coils (e.g., between adjacent wires). In some aspects, wire(s) 490 may be arranged at least partially transverse or perpendicular to a longitudinal axis of device 104 (FIGS. 1A-1E), and rib(s) 492 may extend from wire(s) 490 at least partially proximally. Similarly, in alternative configurations, rib(s) 492 may extend distally so as to reduce or close the gap between each of the spirals or coils. Additionally or alternatively, rib 492 may extend radially outward from wire 490 at different lengths. For example, rib 492 may be longer, or extend further away (e.g., radially outward) from wire 490, for a first length of wire 490, and rib 492 may be shorter, or not extend as far away (e.g., a shorter radially outward distance) from wire 490, for a second length of wire 490. Rib 492 may extend from an entire length of wire 490 or may extend from one or more portions of wire 490.

Referring back to FIG. 1B, in some embodiments, distal end 112 of distal portion 116 may include one or more characteristics or components to facilitate the capturing and/or enclosing of object 160. Although not shown, distal end 112 may include, for example, one or more grasping features such as one or more projections, barbs, extensions, etc. extending radially inward. In some embodiments, the projections(s) may extend radially inward and in a proximal direction. The projection(s) (not shown) may, assist in preventing the distal movement of object 160, for example, once object 160 is within lumen 107 of device 104.

In some instances, however, object 160 may be too large or a user may be incapable of at least partially surrounding or encompassing object 160 within device 104. In such an example, object 160 may remain distal of distal end 112. Method 200 may include optional step 208, in which object 160 may be fragmented, or broken up, outside of device 104, forming object fragments 160'. To be described in further detail below with respect to an optional step 214, for example, optional step 208 may include delivering and activating an energy delivery device 140 within lumen 150. Activating energy delivery device 140 may result in object 160 being fragmented or broken apart forming object fragments 160'. In such a way, the energy delivery device 140 may be activated one or more times, for example, to direct energy towards object 160 and/or object fragments 160'. Once object 160 is fragmented or broken up, for example, to fit within lumen 107 of device 104, object fragments 160' may be pulled or otherwise urged proximally using any of the devices or application of suction, as previously described. Alternatively or additionally, optional step 210 may be repeated such that device 104 may be repositioned or advanced distally to surround object fragments 160'. The user may then proceed as described below.

Additionally, method 200 may include another optional step 210, in which device 104 may be repositioned within lumen 150. For example, during or after the removal of tube 102 and/or before, during, or after the insertion of scope 130, device 104 may be repositioned such that object 160 is partially or completely within (e.g., radially surrounded by) lumen 107. In some aspects, the one or more illumination devices on scope 130 may help the user in visualizing the positions of device 104 and object 160, helping the user to position or reposition device 104 and/or object 160 such that object 160 is at least partially within lumen 107 of device 104. Device 104 may be repositioned by pushing device 104 in a distal direction. For example, a user may push on proximal end 110 to move device 104 in a distal direction. Additionally or alternatively, the internal surface of device 104 may comprise feature(s) 145 extending radially inward, as previously described. In this aspect, a distal end of scope 130 may be used to push against, or abut, the feature(s) 145 to move device 104 in a distal direction. Additionally or alternatively, another medical device (not shown) could be delivered through an internal lumen of scope 130. The other medical device (not shown) could be used to grasp device 104 and distally advance one or more portions of device 104.

Figure 1C:
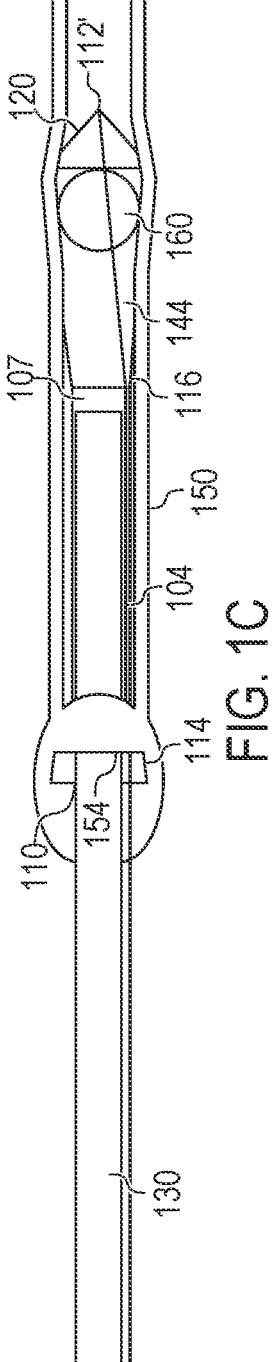

As shown in FIGS. 1C and 2, when object 160 is partially or completely within lumen 107, method 200 includes a step 212, in which a distalmost portion 120 of distal portion 116 is closed. For example, closing distalmost portion 120 may be similar to cinching a pouch or a bag. In the closed configuration, distal end 112 of distal portion 116 may form a tip or a point 112'. For example, in the closed configuration, distal sections of the walls forming distalmost portion 120 of distal portion 116 may taper radially inward towards point 112'. As discussed above, proximal sections of the walls forming distal portion 116 may taper radially inward towards intermediate portion 118.

Distalmost portion 120 may be closed by pulling one or more pull lines 144, for example, by pulling pull line(s) 144 in a proximal direction. Pull line(s) 144 may be coupled to distal end 112 and, for example, surround at least a portion of a circumference of the distalmost portion 120. Pull line(s) 144 may extend proximally through lumen 107 or may extend around the radial exterior of device 104. In another aspect, device 104 may comprise an additional lumen (not shown), for example, in the wall of device 104, extending from proximal end 110 to distal end 112 through which pull line(s) 144 may extend. Pull line(s) 144 may have a loose proximal end extending proximally past proximal end 110. The loose proximal end may enable a user to grasp and pull on pull line(s) 144 proximally, thus closing distalmost portion 120. For example, pulling proximally on pull line(s) 144 causes the closure of distalmost portion 120.

Figure 1D:
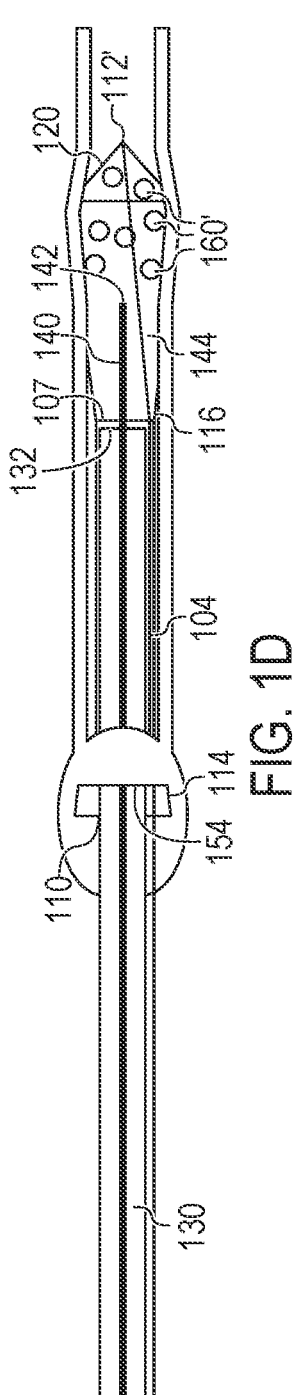

Before, during, or after distalmost portion 120 is closed, method 200 may include an optional step 214, in which an energy delivery device (e.g., an electrohydraulic lithotripsy (EHL) probe or a laser) 140 is inserted through scope 130, as shown in FIG. 1D. Energy delivery device 140 may be inserted such that a distal end 142 of the probe is distal to a distal end 132 of scope 130 and proximal to object 160. In some examples, energy delivery device 140 may be inserted into device 104 without scope 130. Energy delivery device 140 may be used to delivery energy, for example. so as to at least partially fragment, or break, object 160. Closing distalmost portion 120 around object 160 before object 160 is fragmented, or broken, into fragments 160' may help to prevent the loss of one or more of the fragments 160', for example, within a distal portion of lumen 150. Accordingly, closing distalmost portion 120 around object 160 before object 160 is fragmented helps to facilitate the retention or containment of object fragments 160' within device 104 once object 160 is fragmented.

After object 160 is broken into object fragments 160', scope 130 and/or energy delivery device 140 may be retracted or removed proximally. Device 104 and object fragments 160' contained, or retained, within device 104 may then be removed from lumen 150.

Figure 1E:
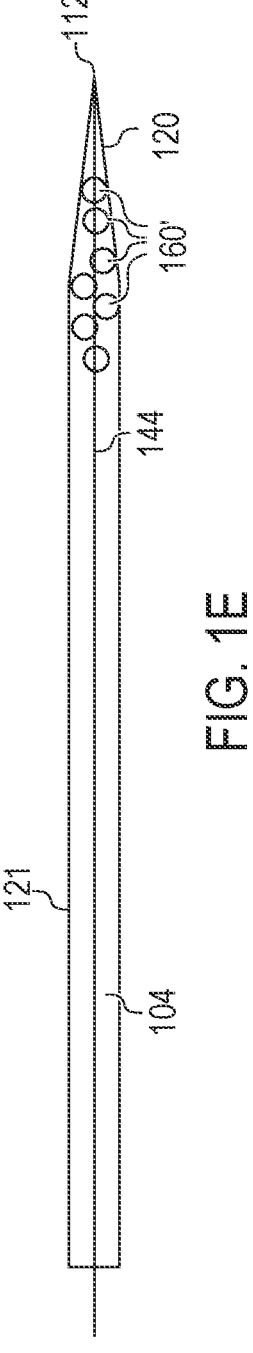

To remove device 104 from lumen 150, for example, in a step 220 of method 200, the user may grasp proximal end 110 using their fingers or a medical device (i.e., forceps, snare, etc.) and pull device 104 proximally. In doing so, device 104 may elongate and the diameter of device 104 may decrease, similar to what is shown in FIG. 1E. For example, proximal portion 114, intermediate portion 118, and distal portion 116 may compress to form a single portion

121. Accordingly, the outer walls of single portion 121 may exert less force against the internal walls of lumen 150, and thus may enable the user to remove device 104 more easily from the subject. Inner walls of device 104 may also assist in the retention of object fragments 160'. Additionally or alternatively, a pull wire (not shown) may extend proximally from a proximal end of device 104. The pull wire (not shown) may be used to facilitate the retraction or removal of device 104 from lumen 150. Upon removal, device 104 may be properly discarded and/or object fragments 160' may be removed for further investigation.

Figure 3:
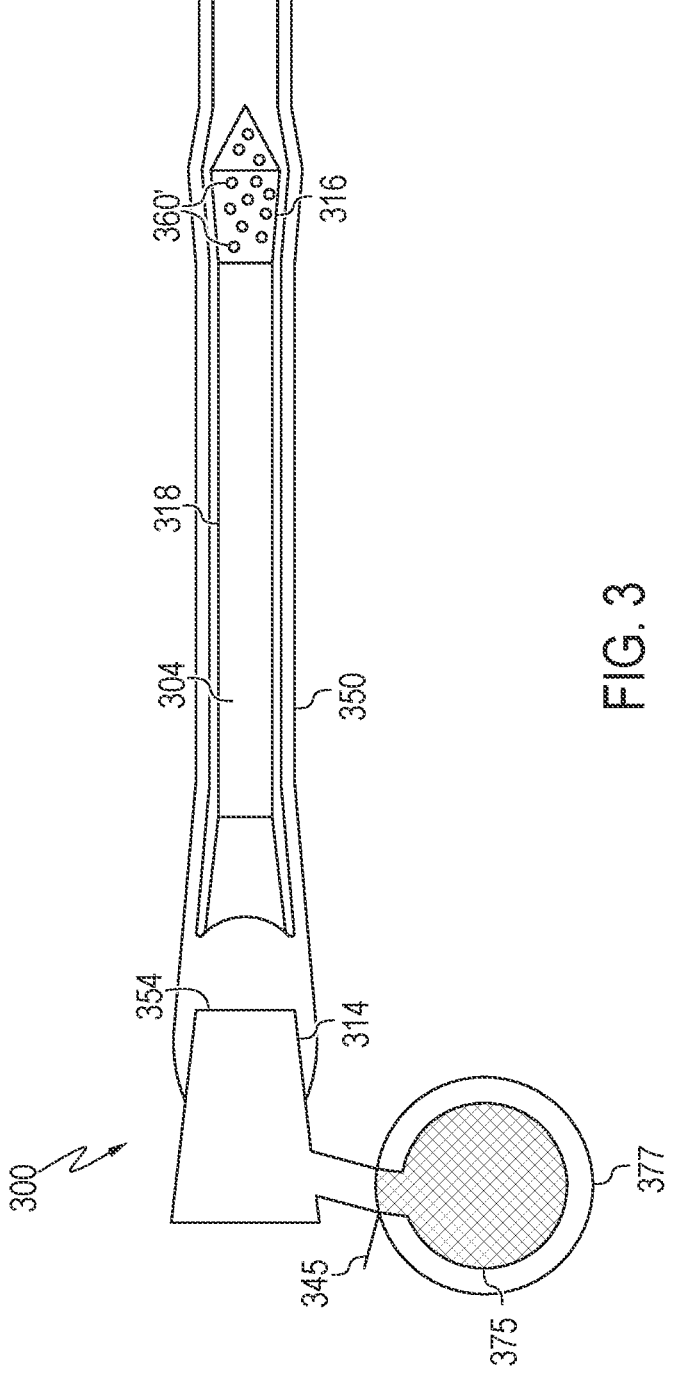
FIG. 3 is a side view of an alternative exemplary medical device, according to aspects of this disclosure.

FIG. 3 illustrates an alternative embodiment of a medical system 300. This embodiment of medical system 300 includes a device 304 that may have any of the characteristics of device 104, except as described below. Medical system 300 may be used to perform one or more steps of method 200, except as described below.

Medical system 300 may be inserted through an opening 354, and may be positioned within a lumen 350 similarly to medical system 100. For example, a tube (not shown) similar to tube 102 described above may be used to deliver and position device 304 within lumen 350. Device 304 may further include a basket 375 extending radially from an external surface of a proximal portion 314 of device 304. For example, basket 375 may be positioned proximal or adjacent to lumen 350 of device 304. In alternative embodiments (not shown), basket 375 may extend radially from an external surface on an intermediate portion 318 or a distal portion 316.

Basket 375 may be positioned outside or inside of the subject. Basket 375 may be used to collect an object and/or object fragments 360' as they are being trawled or otherwise removed from lumen 350. For example, object fragments 360' may be deposited into basket 375 during the procedure. Basket 375 may be comprised of any material commonly used in the art to produce medical baskets. For example, basket 375 may be comprised of a cloth, a mesh, a plastic, or any combination thereof. Basket 375 may additionally or alternative be comprised of an at least partially porous membrane. Alternatively or additionally, basket 375 may include an additional external layer of material such as, for example, a sealed bag 377. The sealed bag 377 may be comprised of, for example, a nonporous material, which may help to prevent leakage. A sealing grommet (not shown) may be positioned proximally to basket 375. The sealing grommet (not shown) may be used to help facilitate the flow of fluids through basket 375 and/or assist with flushing, for example, the object and/or object fragments 360' into basket 375.

Basket 375 may further include one or more pull line(s) 345 that may be used to close or cinch off basket 375 from device 304. For example, when pull line(s) 345 are pulled or otherwise urged proximally, a portion of the basket may be closed or cinched off. One or more tubes (not shown) may extend from and be in fluid connection with sealed bag 377. The one or more tubes (not shown) may be used for aspiration and/or a saline flush. The aspiration and/or saline flush may assist the user with flushing the object fragments 360' from lumen 350. For example, as the object fragments 360' are flushed from lumen 350, object fragments 360' may be captured by basket 375. Excess fluids may flow through basket 375 and be captured by sealed bag 377.

FIG. 5 illustrates an alternative embodiment of a distal portion 516 of a device 504. Device 504 of this embodiment may have any of the characteristics of device 104, except as described below. Additionally, device 504 may be used to perform one or more steps of method 200, except as described below.

In this embodiment, distal portion 516 may comprise one or more characteristics or components to facilitate the capturing and/or enclosing of object 560. Distal portion 516 may comprise, for example, one or more grasping features 517. The grasping feature(s) 517 may comprise one or more wires or hooks extending distally from a distal end 512 of an intermediate portion 518 of device 504. In some embodiments, a distal end of the grasping feature(s) may further comprise a loop or, for example, an eyelet 519a, 519b, 519c. Although three eyelets 519a, 519b, 519c are shown in FIG. 5, alternative configurations may include two, four, five, etc. eyelets. One or more eyelet(s) 519a, 519b, 519c may curl or bend radially inward or radially outward. A pull line 544 may extend through each of the eyelets 519a, 519b, 519c, for example, in sequence. For example, pull line 544 may begin in eyelet 519a, and then extend through eyelet 519b, then 519c, etc. A proximal end of pull line 544 may extend proximally through lumen 507 of device 504 such that, in a second configuration, for example, when object 560 is partially or completely within lumen 507, pull line 544 may be pulled or otherwise urged proximally to close or purse down the distalmost end of device 504. In an alternative configuration (not shown), pull line 544 may extend around the radial exterior of device 504.

In further alternative embodiments, a covering 523 may extend between one or more of grasping feature(s) 517. Covering 523 may comprise one or more materials such as, for example, a netting, a silicone material, a mesh material, or any combination thereof. In some embodiments, covering 523 may help to allow fluids to escape or otherwise flow out of device 504, while helping to maintain object 560 within lumen 507.

Figures 6A, 6B:
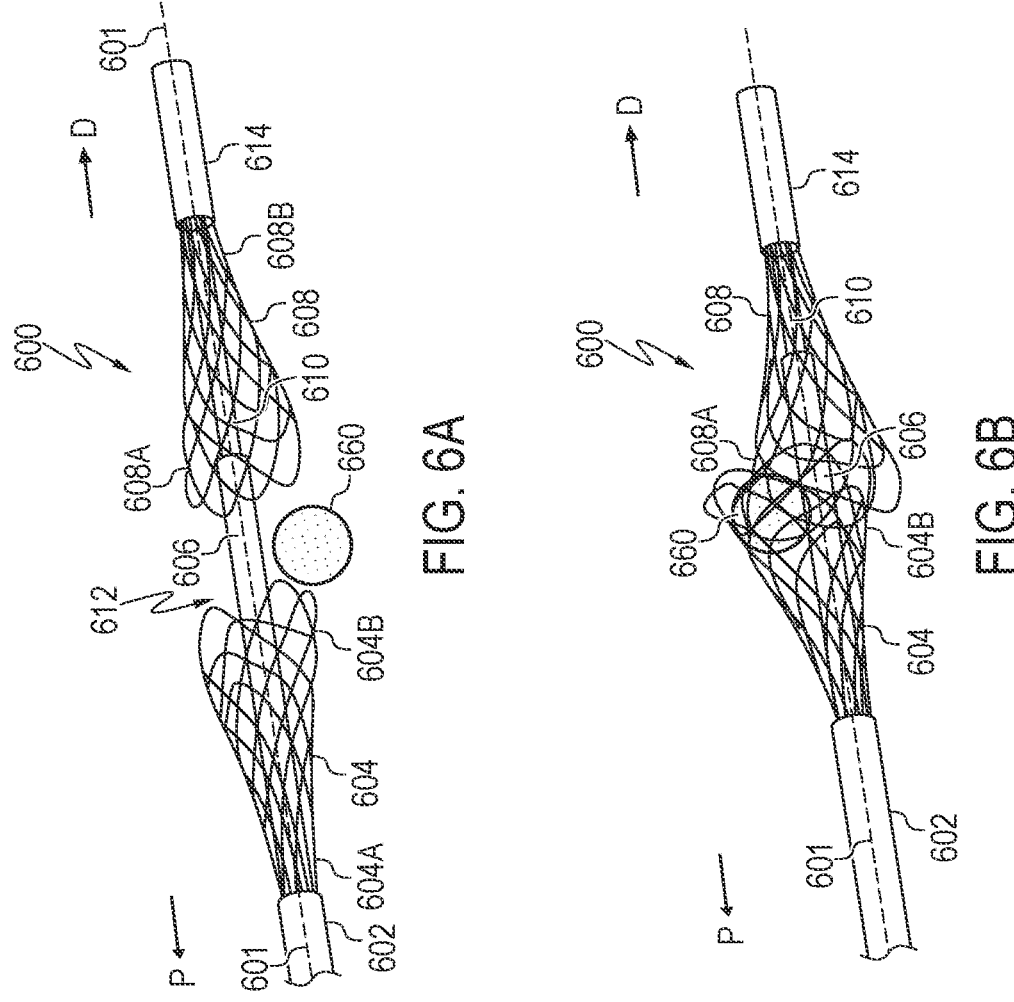
FIGS. 6A and 6B are perspective views of an exemplary medical device in an open configuration (FIG. 6A) and in a closed configuration (FIG. 6B), according to aspects of this disclosure.

FIGS. 6A and 6B illustrate an alternative embodiment of a deployed exemplary medical device 600 in an open configuration (FIG. 6A) and in a closed configuration (FIG. 6B). Device 600 may include a proximal basket 604 and a distal basket 608.

Proximal basket 604 and distal basket 608 may be formed of one or more flexible or semi-flexible materials, such as, for example, plastic, Nitinol, stainless steel, elgiloy (e.g., a non-magnetic Cobalt-Chromium-Nickel-Molybdenum alloy), one or more shape-memory polymers, or any material commonly known in the art. Additionally or alternatively, proximal basket 604 and distal basket 608 may be formed similar to a stent and be comprised of, for example, woven threads or wires, mesh, fabric, silicone, or any combination thereof. Proximal basket 604 and distal basket 608 may be formed of the same material. Alternatively, proximal basket 604 and distal basket 608 may be formed of different materials having different characteristics, or of the same material having different characteristics. For example, if proximal basket 604 is comprised of woven Nitinol threads or wires, in a similar manner as a stent, the threads or wires forming proximal basket 604 may differ in size and/or pitch in comparison to the threads or wires forming distal basket 608. Many other combinations are also possible.

A proximal portion 604A of proximal basket 604 may be coupled to an external surface of an internal sheath 606. Proximal basket 604 may be coupled to internal sheath 606, for example, by one or more fasteners or adhesives. For example, proximal basket 604 may be coupled to internal sheath 606 by one or more glue(s), heat shrink(s), crimp(s), etc.

Internal sheath 606 may extend through a center of proximal basket 604, for example, along a longitudinal axis 601. Proximal basket 604 may partially or completely extend about, or around, internal sheath 606. A distal portion 604B of proximal basket 604 may be loose, or unsecured, from internal sheath 606, such that, in the deployed configuration shown in FIGS. 6A and 6B, distal portion 604B of proximal basket 604 expands radially outward. Accordingly, when proximal basket 604 is in the deployed configuration, a distal opening of proximal basket 604 is oriented in a distal direction.

A distal portion of internal sheath 606 may extend through a proximal portion 608A of distal basket 608. A distal portion 608B of distal basket 608 may be coupled to an external surface of a control wire 610. Distal basket 608 may be coupled to control wire 610, for example, by one or more fasteners or adhesives. For example, distal basket 608 may be coupled to control wire 610 by one or more glue(s), heat shrink(s), crimp(s), etc. In some embodiments, a distal sheath 614 may partially or completely extend about, or around, distal portion 608B of distal basket 608. For example, distal sheath 614 may be similar to a cap. In alternative configurations, although not shown, control wire 610 may extend through a center of distal sheath 614 such that a distal portion of control wire 610 may extend past a distal end of distal sheath 614.

Control wire 610 may extend through a center of distal basket 608, for example, along a longitudinal axis 601. For example, distal basket 608 may partially or completely extend about, or around, control wire 610. A proximal portion 608A of distal basket 608 may be loose, or unsecured, from control wire 610, such that, in the deployed configuration shown in FIGS. 6A and 6B, proximal portion 608A of distal basket 608 expands radially outward. Accordingly, when distal basket 608 is in the deployed state, a proximal opening of the distal basket 608 is oriented in a proximal direction.

Control wire 610 may extend from a proximal end of device 600 to a distal end of device 600. For example, control wire 610 may extend from the proximal end to the distal end of device 600 through a lumen of internal sheath 606. Control wire 610 may be independently movable relative to internal sheath 606. For example, when control wire 610 is extended distally relative to internal sheath 606, internal sheath 606 may remain in place. Although not shown, a proximal portion of control wire 610 may be coupled to an actuator on a handle such that, for example, when the actuator in the handle is actuated, control wire 610 and distal basket 608 may be retracted proximally or extended distally relative to internal sheath 606.

Similarly, internal sheath 606 may extend from a proximal end of device 600 to a distal end of device 600 though a lumen of an external sheath 602. Internal sheath 606 may be independently movable relative to external sheath 602. For example, when internal sheath 606 is retracted proximally or advanced distally relative to external sheath 602, external sheath 602 may remain in place. In some embodiments, internal sheath 606 may be extended or moved distally relative to external sheath 602 to deploy one or more proximal basket 604 and distal basket 608. Although not shown, a proximal portion of internal sheath 606 may be coupled to a second actuator on the handle such that, for example, when the second actuator in the handle is actuated, internal sheath 606 and proximal basket 604 may be retracted proximally or advanced distally. Additionally or alternatively, in such a configuration, a proximal portion of external sheath 602 may be coupled to the handle.

Alternatively, external sheath 602 may be independently movable relative to internal sheath 606. For example, when external sheath 602 is retracted proximally or advanced distally relative to internal sheath 606, internal sheath 606 may remain in place. For example, retracting or moving external sheath 602 proximally relative to internal sheath 606 may deploy one or more proximal basket 604 and distal basket 608. In such a configuration, a proximal portion of external sheath 602 may instead be coupled to the second actuator in the handle such that, for example, when the second actuator in the handle is actuated, external sheath 602 may be moved proximally or distally relative to internal sheath 606.

One or more of external sheath 602, internal sheath 606, and distal sheath 614 may each be formed of one or more flexible or semi-flexible material(s) such as, for example, plastic, polyvinyl chloride (PVC), polyethylene, thermoplastic elastomers (TPE), nylon, silicone, etc. In some configurations, external sheath 602 may be clear or translucent to help a user visualize a position of the proximal basket 604 and/or distal basket 608.

One or more components of device 600, for example, one or more external sheath 602, proximal basket 604, internal sheath 606, distal basket 608, and/or control wire 610, may comprise or be comprised of materials such that a user may visualize a position of each of the one or more components of device 600 during medical imaging, for example, fluoroscopy, X-ray imaging, magnetic resonance imaging (MRI), ultrasonography, computer tomography (CT) imaging, etc. Additionally or alternatively, in a similar manner, the one or more components of device 600 may comprise one or more radiopaque markers to enable the user to visualize the position of the one or more components of device 600. For example, the material(s) or marker(s) may be used to position the one or more components of device 600 relative to an object 660. For example, the user may wish to position distal basket 608 distally of object 660.

In a non-deployed configuration (not shown) of device 600, external sheath 602 may extend about, or around, proximal basket 604, internal sheath 606, distal basket 608, and control wire 610. For example, proximal basket 604, internal sheath 606, distal basket 608, and control wire 610 may be confined within a lumen of external sheath 602. External sheath 602 may extend distally beyond a distalmost portion of distal basket 608 and/or control wire 610, for example, to confine the other components of device 600. Device 600 may be in the non-deployed state, for example, during the insertion and/or positioning of device 600 into a cavity or a lumen.

In some configurations, external sheath 602 may be retracted or pulled proximally to deploy, or release, proximal basket 604 and distal basket 608. In alternative configurations, distal basket 608 may be confined within the lumen of internal sheath 606 such that, when external sheath 602 is retracted or pulled proximally, only proximal basket 604 is deployed or released. In such a configuration, distal basket 608 may be deployed or released by extending or pushing control wire 610 distally relative to internal sheath 606.

As shown in FIG. 6A, once proximal basket 604 and distal basket 608 are deployed or released, an opening or gap 612 may separate proximal basket 604 from distal basket 608. For example, gap 612 separating proximal basket 604 from distal basket 608 may be large or wide enough such that a distal portion 604B of proximal basket 604 is proximal or adjacent to a proximalmost portion of object 660 and proximal portion 608A of distal basket 608 is distal or adjacent to a distalmost portion of object 660. In some instances, the user may manipulate control wire 610 to position distal basket 608 and/or proximal basket 604 relative to object 660. For example, the user may position object 660 within or adjacent to gap 612. Additionally or alternatively, internal sheath 606 and control wire 610 may each be comprised of one or more flexible material(s) such that internal sheath 606 and/or control wire 610 may be axially offset from longitudinal axis 601. For example, internal sheath 606 and/or control wire 610 may be positioned against a wall of the lumen. Offsetting internal sheath 606 and/or control wire 610, for example, may facilitate the ability for device 600 to maneuver around and/or capture object 660. For example, offsetting internal sheath 606 and/or control wire 610 may enable the user to maneuver around and/or capture a larger object 660.

Additionally or alternatively, distal portion 604B of proximal basket 604 and/or proximal portion 608A of distal basket 608 may be axially offset from internal sheath 606, control wire 610, and/or longitudinal axis 601. Axially offsetting distal portion 604B of proximal basket 604 and/or proximal portion 608A of distal basket 608 may further facilitate the ability for device 600 to maneuver around and/or capture object 660. For example, offsetting distal portion 604B of proximal basket 604 and/or proximal portion 608A of distal basket 608 may enable the user to maneuver around and/or capture a larger object 660.

As shown in FIG. 6B, proximal basket 604 may be moved or advanced distally by extending internal sheath 606, and/or distal basket 608 may be retracted or pulled proximally by retracting or pulling control wire 610 proximally. Accordingly, gap 612 may be reduced or eliminated. For example, the distalmost portion of proximal basket 604 may abut or touch the proximalmost portion of distal basket 608. Accordingly, object 660 may be captured within each of the proximal basket 604 and distal basket 608. Device 600 and object 660 may then be removed from the subject. In some configurations, distal portion 604B of proximal basket 604 and proximal portion 608A of distal basket 608 may at least partially overlap, for example, to assist in enclosing object 660. For example, an overlap of distal portion 604B of proximal basket 604 and proximal portion 608A of distal basket 608 may enable a decreasing diameter of distal basket 608 as sheath 602 is extended over proximal basket 604. Such a configuration may facilitate a decreased outer diameter of device 600 for removal from the subject. Similarly, object 660 may be fragmented before being captured within each of the proximal basket 604 and distal basket 608. Fragmenting object 660 may assist with further decreasing the outer diameter of device 600 for removal from the subject.

Figures 7A, 7B:
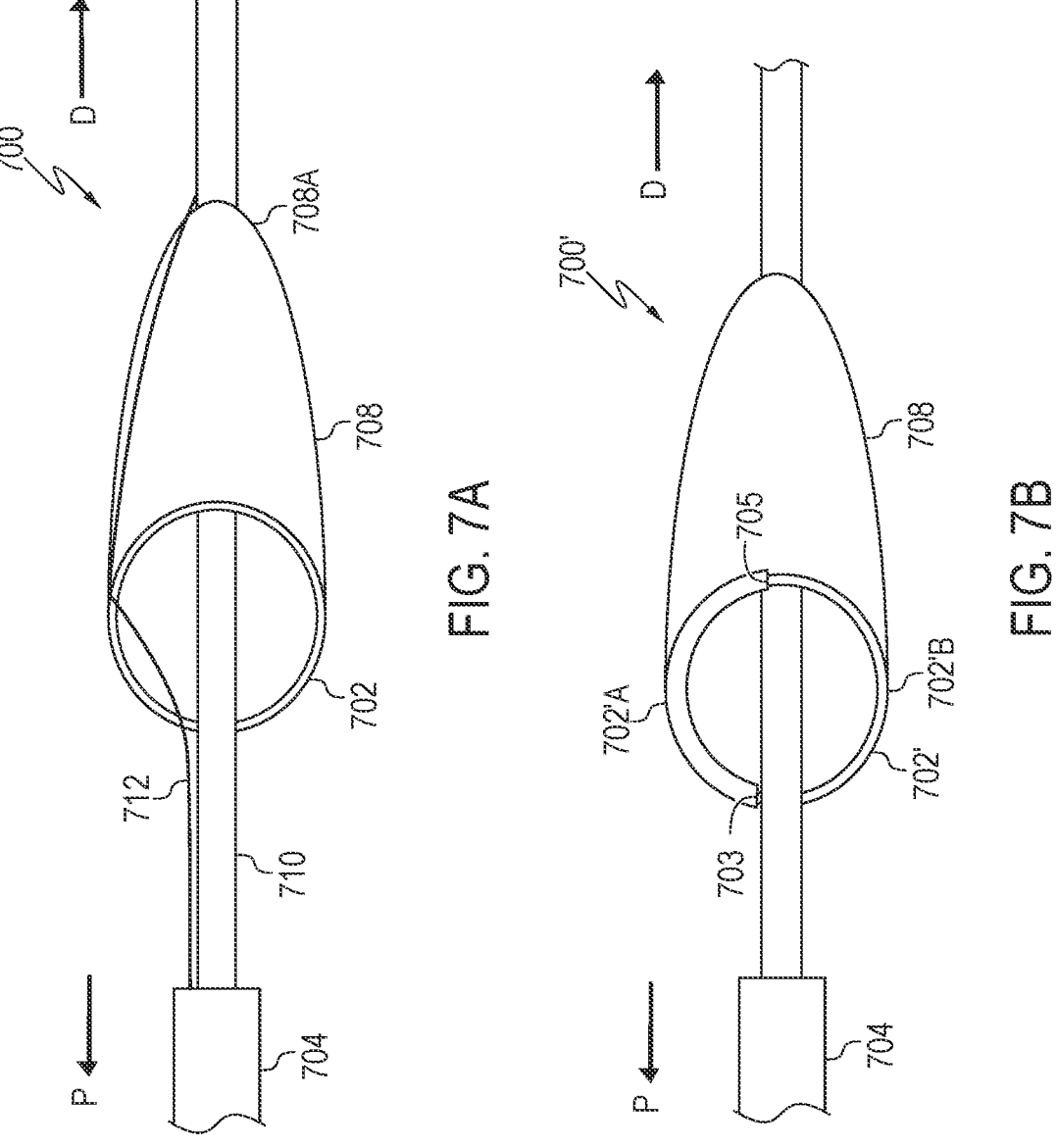
FIGS. 7A and 7B are perspective views of alternative configurations of an exemplary medical device, according to aspects of this disclosure.

FIG. 7A illustrates an alternative embodiment of a deployed exemplary medical device 700. Device 700 may comprise a flexible or semi-flexible wire 710. Wire 710 may extend through a ring 702 and a basket 708. As shown in FIGS. 7A and 7B, wire 710 may extend through an entirety of basket 708, for example, through a distal portion 708A of basket 708. Alternatively, wire 710 may be coupled to an internal wall (not shown) comprising distal portion 708A of basket 708. Wire 710 may be coupled to the internal wall of basket 708 by one or more adhesive(s) and/or mechanical fastener(s). Additionally or alternatively, wire 710 may be coupled to ring 702 and/or a portion of basket 708 such that wire 710 is oriented off-axis from the body lumen. In this configuration, for example, a proximal opening of basket 708 may be larger to facilitate capturing or maneuvering around an object (not shown).

Ring 702 may form the proximal opening of basket 708. Ring 702 may be formed of one or more flexible or semi-flexible materials, such as, for example, plastic, Nitinol, stainless steel, elgiloy (e.g., a non-magnetic Cobalt-Chromium-Nickel-Molybdenum alloy), shape-memory polymers, or any material commonly known in the art. Ring 702 may be circular, ovular, elliptical, square, rectangular, pentagonal, etc. In some configurations, ring 702 may be configured so as to fill the diameter of the lumen upon deployment. In some aspects, ring 702 may be irregularly shaped.

Basket 708 may be coupled to ring 702. For example, a proximal portion of basket 708 may be coupled to an outer or an inner diameter of ring 702. Basket 708 may be formed similar to a stent and/or be comprised of, for example, woven threads or wires, mesh, fabric, silicone, or any combination thereof. Additionally or alternatively, basket 708 (or one or more portions of basket 708) may comprise a flexible porous membrane and/or may comprise a shape-memory material. The material(s) forming basket 708 may help to maintain a shape of basket 708 and/or to help prevent one or more portions of basket 708 from collapsing. In some configurations, basket 708 may be formed around ring 702. For example, ring 702 may be woven into basket 708.

In some configurations, medical device 700 may comprise more than one ring 702. For example, two, three, four, or more rings 702 may be oriented or spaced along the length of basket 708. The additional rings 702 may be similarly sized or may include a variety of shapes and sizes. For example, a ring 702 in a proximal portion of basket 708 may be larger (e.g., have a greater diameter) than a ring 702 in a distal portion of basket 708, or vice versa, in order to form a tapered configuration of basket 708.

In some configurations, device 700 may include a control wire 712. Control wire 712 may extend through a lumen of an external sheath 704 (e.g., from a proximal end to a distal end). In alternative configurations, control wire 712 may extend externally to external sheath 704 (as shown in FIG. 7A). A proximal end of control wire 712 may comprise a free end (not shown) or may be coupled to a handle (not shown) to assist in pulling control wire 712 proximally or pushing control wire 712 distally. A distal end of control wire 712 may be coupled to a distalmost portion of wire 710 such that, for example, at least a portion of each of ring 702 and basket 708 are between wire 710 and control wire 712. Accordingly, as control wire 712 is pulled or otherwise urged proximally, ring 702 and basket 708 may collapse against wire 710. This may enable a user to more easily extend and/or retract external sheath 704 around ring 702 and/or basket 708 and/or assist in the removal of device 700 from the subject. Additionally or alternatively, distal movement of control wire 712 may expand ring 702 and basket 708.

Although one control wire 712 is shown, alternative configurations may comprise two, three, four, or more control wires 712. Additional control wires 712 may be positioned around ring 702 and basket 708 such that, when the control wires 712 are pulled or otherwise urged proximally ring 702 and basket 708 are collapsed more evenly against wire 710. Similarly, additional control wires 712 may assist in the expansion of ring 702 and basket 708.

In a non-deployed configuration (not shown) of device 700, an external sheath 704 may extend about, or around, ring 702 and basket 708. For example, ring 702 and basket 708 may be within a lumen of external sheath 704. External sheath 704 may be retracted or pulled proximally, and/or wire 710 may be extended or advanced distally to deploy ring 702 and basket 708 from external sheath 704.

FIG. 7B illustrates an alternative embodiment of a deployed exemplary medical device 700'. For example, FIG. 7B illustrates an alternative configuration for ring 702 of device 700'. Similar to device 700, a ring 702' may form a proximal opening of basket 708. In this configuration, ring 702' may be adjustable. For example, ring 702' may be comprised of at least two sections 702'A and 702'B. One or more joint(s) 703 may couple section 702'A to section 702'B. For example, joint(s) 703 may comprise a hinge, a swivel, a pivot, a bend, etc., so as to permit movement of section 702'B relative to section 702'A, or vice versa. Joint(s) 703 may be spring-loaded. A portion of section 702'A may be configured to receive a section of 702'B, for example, at an end 705 of section 702'A. Accordingly, the diameter of ring 702' may be adjustable. For example, section 702'A may comprise a cavity (not shown) and have a larger cross-sectional diameter than a cross-sectional diameter of section 702'B. The cavity (not shown) may be sized to receive section 702'B, for example, at end 705 of section 702'A. Accordingly, when section 702'B is received by section 702'A, the diameter of ring 702' may decrease. When portion 702'B is released from portion 702'A, the diameter of ring 702' may increase.

Basket 708 may be coupled to ring 702'. For example, a proximal portion of basket 708 may be coupled to section(s) 702'A and/or 702'B. In some configurations, basket 708 may be formed around ring 702'. For example, section(s) 702'A and/or 702'B may be woven into basket 708.

Similar to device 700, in a non-deployed configuration (not shown) of device 700', an external sheath 704 may extend about, or around, ring 702' and basket 708. For example, ring 702' and basket 708 may be within a lumen of external sheath 704. External sheath 704 may be retracted or pulled proximally, and/or wire 710 may be extended or advanced distally to deploy ring 702' and basket 708 from external sheath 704.

The movement of section 702'B to section 702'A, or vice versa, may be controlled by, for example, the natural movement of the lumen. For example, as the lumen increases in diameter, ring 702' may increase in diameter as described above. Likewise, as the lumen decreases in diameter, ring 702' may decrease in diameter as described above. Although not shown, device 700' may comprise one or more control wire(s) having the same characteristics as control wire 712 of device 700, shown in FIG. 7A. For example, the control wire(s) (not shown) may be coupled to section 702'A and/or 702'B and may facilitate the expansion and/or collapse of ring 702' and basket 708.

In the embodiments shown in FIGS. 7A and 7B, devices 700 and 700' may be used to capture an object (not shown) within a lumen, for example, within basket 708. For example, rings 702 and 702' may be placed distally relative to object. Once rings 702 and 702' and basket 708 are released or deployed from external sheath 704, devices 700 and 700' may be retracted or pulled proximally to capture the object within basket 708. Once the object is captured, devices 700 and 700' may be removed from the subject.

Figures 8A, 8B:
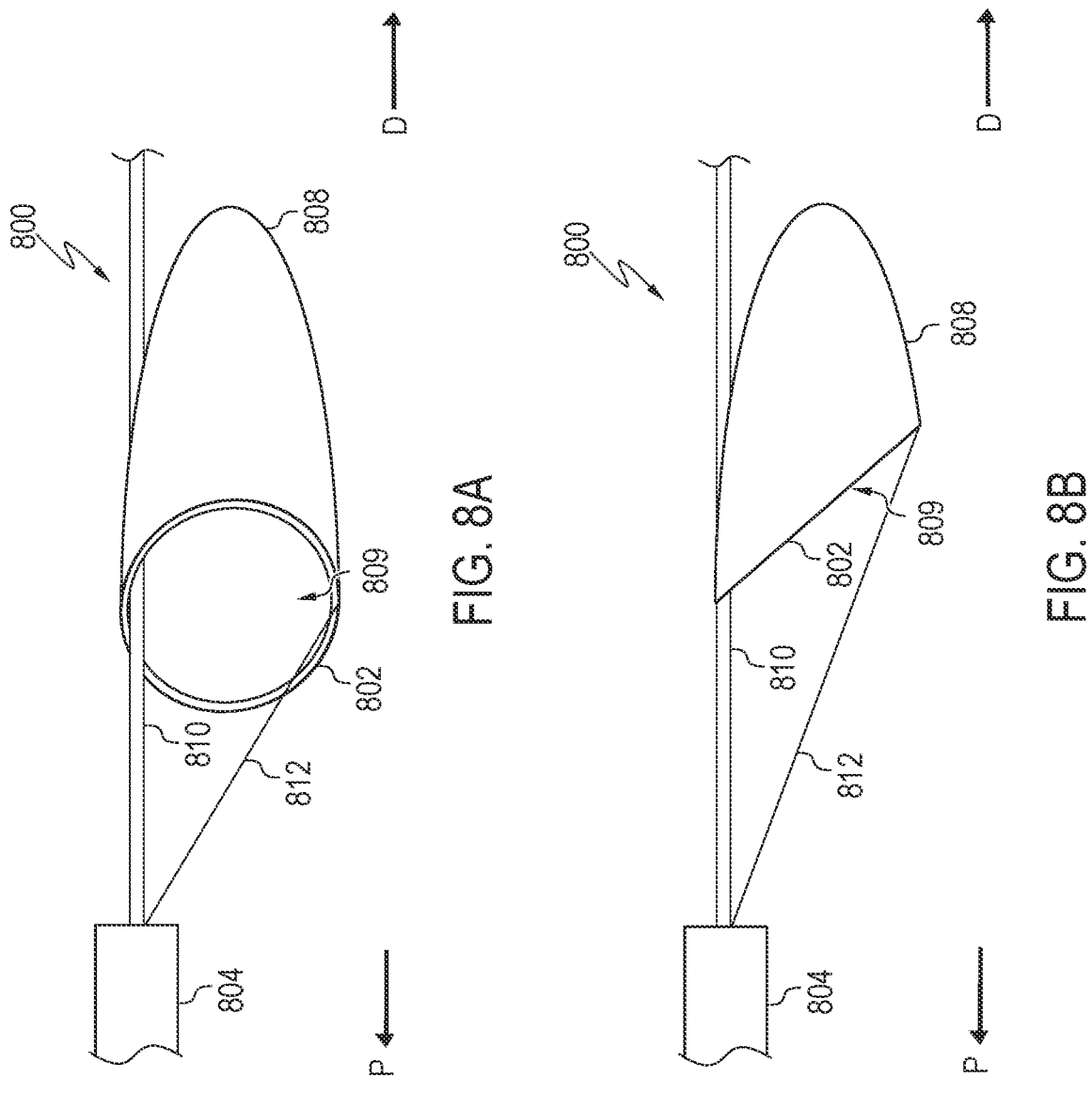
FIG. 8A is a perspective view of an exemplary medical device.
FIG. 8B is a side view of the exemplary medical device, according to aspects of this disclosure.

FIGS. 8A and 8B illustrate an alternative embodiment of a deployed exemplary medical device 800. Device 800 may include a basket 808 and a ring 802, which may have any of the characteristics of basket 708 and ring 702 or 702' of device 700 and/or 700', except as described below. Additionally, device 800 may comprise a flexible or semi-flexible wire 810 having any of the characteristics of device 700 and/or 700'. For example, as shown in FIGS. 8A and 8B, wire 810 may extend through an entirety of basket 808. Alternatively, wire 810 may be coupled to an internal wall (not shown) comprising basket 808. Wire 810 may be coupled to the internal wall of basket 808 by one or adhesive(s) and/or mechanical fasteners.

A distal end of a control wire 812 may be coupled to ring 802. Control wire 812 may extend through a lumen of an external sheath 804 (e.g., from a proximal end to a distal end). In alternative configurations, control wire 812 may extend externally to external sheath 804. A proximal end of control wire 812 may comprise a free end (not shown) or may be coupled to a handle (not shown) to assist in pulling control wire 812 proximally or pushing control wire 812 distally.

As shown in FIG. 8A, the distal end of control wire 812 may be coupled to a portion of ring 802. For example, control wire 812 may be coupled to a portion of ring 802 opposite from the position of wire 810 relative to ring 802. Alternatively, control wire 812 may be coupled to ring 802 in one or more other positions. For example, control wire 812 may be coupled to one or more sides of ring 802. In some configurations, control wire 812 may enable a user to maneuver, open, and/or close a proximal opening of basket 808.

As shown in FIG. 8B, a proximal opening 809 of basket 808 may be angled relative to control wire 810. For example, a portion of proximal opening 809 opposite to wire 810 may be more distal to an upward portion of proximal opening 809. As control wire 812 is pulled or otherwise urged proximally, the portion of the proximal opening 809 opposite to wire 810 may also be pulled or otherwise urged proximally such that the portion of the proximal opening 809 opposite to wire 810 is more proximal to the portion of proximal opening 809 adjacent to wire 810. In this movement, basket 808 may be used to "scoop" an object (not shown) into basket 808. Additionally, because wire 810 is offset from the center of basket 808 and/or because the proximal opening 809 is angled relative to control wire 810, proximal opening 809 may be larger to facilitate the capture of a larger object (not shown).

Figure 9:
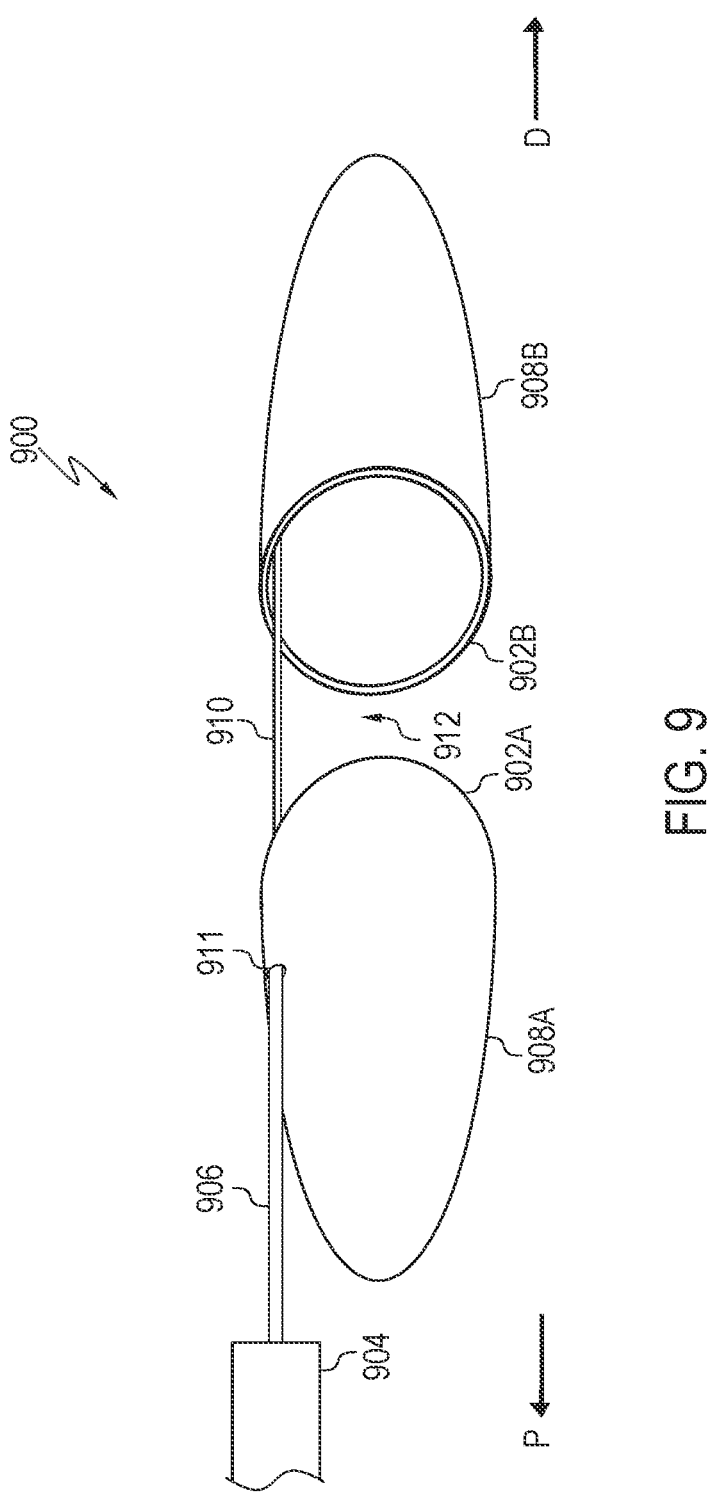
FIG. 9 is a perspective view of another exemplary medical device, according to aspects of this disclosure.

FIG. 9 illustrates an alternative embodiment of a deployed exemplary medical device 900 in an open configuration. Device 900 may include a proximal basket 908A and a distal basket 908B. Proximal basket 908A and distal basket 908B may be oriented in a similar manner as proximal basket 604 and distal basket 608 of device 600, shown in FIGS. 6A and 6B. Proximal basket 908A and distal basket 908B may have any of the characteristics of the basket 708 in FIGS. 7A and 7B, and/or basket 808 in FIGS. 8A and 8B. Additionally, device 900 may include a proximal ring 902A and a distal ring 902B that may have any of the characteristics of one or more of ring 702 in FIG. 7A, ring 702' in FIG. 7B, and/or ring 802 in FIGS. 8A and 8B.

Proximal basket 908A and distal basket 908B may be formed of the same material. Alternatively, proximal basket 908A and distal basket 908B may be formed of different materials having different characteristics, or of the same material having different characteristics. For example, if proximal basket 908A is comprised of woven Nitinol threads or wires, in a similar manner as a stent, the threads or wires forming proximal basket 908A may differ in size and/or pitch in comparison to the threads or wires forming distal basket 908B. Many other combinations are also possible.

An internal sheath 906 may extend through a portion of basket 908A. For example, internal sheath 906 may extend through a hole 911 on an external surface of proximal basket 908A. A portion of proximal basket 908A may be coupled to an external surface of internal sheath 906 such that proximal basket 908A moves (e.g., proximally and/or distally) with movement of internal sheath 906. Proximal basket 908A may be coupled to internal sheath 906, for example, by one or more fasteners or adhesives. For example, proximal basket 908A may be coupled to sheath 906 by one or more glue(s), heat shrink(s), crimp(s), etc. Proximal basket 908A may partially or completely extend about, or around, internal sheath 906. A proximal portion of proximal basket 908A may be loose, or unsecured, from internal sheath 906. Accordingly, when proximal basket 908A is in the deployed configuration, ring 902A may expand and a distal opening of proximal basket 908A is oriented in a distal direction.

A portion of distal basket 908B may be coupled to an external surface of a control wire 910. Distal basket 908B may be coupled to control wire 910, for example, by one or more fasteners or adhesives. For example, distal basket 908B may be coupled to control wire 910 by one or more glue(s), heat shrink(s), crimp(s), etc. In some configurations, although not shown, control wire 910 may extend through distal basket 908B such that a distal portion of control wire 910 may extend past a distal portion of distal basket 908B. For example, distal basket 908B may partially or completely extend about, or around, control wire 910. Accordingly, when distal basket 908B is in the deployed state, ring 902B may expand and a proximal opening of the distal basket 908B may be oriented in a proximal direction.

Control wire 910 may extend from a proximal end of device 900 to a distal end of device 900. For example, control wire 910 may extend from the proximal end to the distal end of device 900 through a lumen of internal sheath 906. Control wire 910 may be independently movable relative to internal sheath 906. For example, when control wire 910 is extended distally relative to internal sheath 906, internal sheath 906 may remain in place. Although not shown, a proximal portion of control wire 910 may be coupled to an actuator on a handle such that, for example, when the actuator in the handle is actuated, control wire 910 and distal basket 908B may be retracted proximally or extended distally relative to internal sheath 906.

Similarly, internal sheath 906 may extend from a proximal end of device 900 to a distal end of device 900 though a lumen of an external sheath 904. Internal sheath 906 may be independently movable relative to external sheath 904. For example, when internal sheath 906 is retracted proximally or advanced distally relative to external sheath 904, external sheath 904 may remain in place. In some embodiments, internal sheath 906 may be extended or moved distally relative to external sheath 904 to deploy one or more proximal basket 908A and distal basket 908B. Although not shown, a proximal portion of internal sheath 906 may be coupled to a second actuator on the handle such that, for example, when the second actuator in the handle is actuated, internal sheath 906 and proximal basket 908A may be retracted proximally or advanced distally. Additionally or alternatively, in such a configuration, a proximal portion of external sheath 904 may be coupled to the handle.

Alternatively, external sheath 904 may be independently movable relative to internal sheath 906. For example, when external sheath 904 is retracted proximally or advanced distally relative to internal sheath 906, internal sheath 906 may remain in place. For example, retracting or moving external sheath 904 proximally relative to internal sheath 906 may deploy one or more proximal basket 908A and distal basket 908B. In such a configuration, a proximal portion of external sheath 904 may instead be coupled to the second actuator in the handle such that, for example, when the second actuator in the handle is actuated, external sheath 904 may be moved proximally or distally relative to internal sheath 906.

One or more of external sheath 904 and internal sheath 906 may each be formed of one or more flexible or semi-flexible material(s) such as, for example, plastic, polyvinyl chloride (PVC), polyethylene, thermoplastic elastomers (TPE), nylon, silicone, etc. In some configurations, external sheath 904 may be clear or translucent to help a user visualize a position of the proximal basket 908A and/or distal basket 908B.

One or more components of device 900, for example, one or more external sheath 904, proximal basket 908A, internal sheath 906, distal basket 908B, and/or control wire 910, may comprise or be comprised of materials such that a user may visualize a position of each of the one or more components of device 900 during medical imaging, for example, fluoroscopy, X-ray imaging, magnetic resonance imaging (MRI), ultrasonography, computer tomography (CT) imaging, etc. Additionally or alternatively, in a similar manner, the one or more components of device 900 may comprise one or more radiopaque markers to enable the user to visualize the position of the one or more components of device 900. For example, the material(s) or marker(s) may be used to position the one or more components of device 900 relative to an object (not shown). For example, the user may wish to position distal basket 908B distally of the object.

In a non-deployed configuration (not shown) of device 900, external sheath 904 may extend about, or around, proximal basket 908A, internal sheath 906, distal basket 908B, and control wire 910. For example, proximal basket 908A, internal sheath 906, distal basket 908B, and control wire 910 may be confined within a lumen of external sheath 904. External sheath 904 may extend distally beyond a distalmost portion of distal basket 908B and/or control wire 910, for example, to confine the other components of device 900. Device 900 may be in the non-deployed state, for example, during the insertion and/or positioning of device 900 into a cavity or a lumen.

In some configurations, external sheath 904 may be retracted or pulled proximally to deploy, or release, proximal basket 908A and distal basket 908B. Alternatively or additionally, internal sheath 906 and/or control wire 910 may be extended distally to deploy, or release, proximal basket 908A and distal basket 908B. In alternative configurations, distal basket 908B may be confined within the lumen of internal sheath 906 such that, when external sheath 904 is retracted or pulled proximally, only proximal basket 908A is deployed or released. In such a configuration, distal basket 908B may be deployed or released by extending or pushing control wire 910 distally relative to internal sheath 906.

As shown in FIG. 9, once proximal basket 908A and distal basket 908B are deployed or released, an opening or gap 912 may separate proximal basket 908A from distal basket 908B. For example, gap 912 separating proximal basket 908A from distal basket 908B may be large or wide enough such that a distal portion of proximal basket 908A is proximal or adjacent to an object (not shown) and a proximal portion of distal basket 908B is distal or adjacent to the object. In some instances, the user may manipulate control wire 910 and/or internal sheath 906 to position distal basket 908B and/or proximal basket 908A relative to the object. For example, the user may position the object within or adjacent to gap 912.

Although not shown, in a closed configuration, proximal basket 908A may be moved or advanced distally by extending internal sheath 906, and/or distal basket 908B may be retracted or pulled proximally by retracting or pulling control wire 910 proximally. Accordingly, gap 912 may be reduced or eliminated. For example, a distalmost portion of proximal basket 908A may abut or touch a proximalmost portion of distal basket 908B. Accordingly, the object or one or more portions of object (not shown) may be captured within one or more of the proximal basket 908A and distal basket 908B. Additionally or alternatively, the object may be sandwiched between proximal basket 908A and distal basket 908B. Device 900 and the object may then be removed from the subject.

In some configurations, the distal portion of proximal basket 908A and the proximal portion of distal basket 908B may at least partially overlap, for example, to assist in enclosing the object within proximal basket 908A and distal basket 908B. For example, an overlap of the distal portion of proximal basket 908A and the proximal portion of distal basket 908B may enable a decreasing diameter of distal basket 908B as external sheath 904 is extended over proximal basket 908A. Such a configuration may facilitate a decreased outer diameter of device 900 for removal from the subject.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

We claim:

1. A method for removing one or more objects or materials from a body lumen, the method comprising:

delivering a tube and an expandable device to the body lumen to a position proximal to the one or more objects or materials, wherein the expandable device is positioned with a lumen of the tube, and wherein the expandable device includes a lumen extending from a distal portion to a proximal portion;

delivering a scope through the lumen of the tube and through the lumen of the expandable device;

proximally retracting the tube such that the expandable device remains in the position proximal to the one or more objects or materials;

distally advancing the expandable device such that the distal portion of the expandable device at least partially surrounds the one or more objects or materials, wherein distally advancing the expandable device includes (1) abutting a distal end of the scope with one or more radially inward extensions on an inner surface of the expandable device, and (2) distally advancing the scope to distally advance the expandable device;

at least partially closing a distal end of the expandable device; and moving the expandable device proximally to remove the expandable device and the one or more objects or materials from the body lumen.

2. The method of claim 1, further comprising, before distally advancing the expandable device, expanding the distal portion of the expandable device with a balloon.

3. The method of claim 1, wherein at least the distal portion of the expandable device is formed of a shape-memory material that expands on its own when no longer positioned within the lumen of the tube.

4. The method of claim 1, wherein at least partially closing the distal end of the expandable device includes proximally retracting one or more pull lines coupled to the distal end of the expandable device.

5. The method of claim 4, wherein proximally retracting the one or more pull lines causes the distal end of the expandable device to taper radially inward to at least partially close the distal end of the expandable device.

6. The method of claim 1, further comprising;

after at least partially closing the distal end of the expandable device, delivering an energy delivery device through the lumen of the tube and the lumen of the expandable device; and activating the energy delivery device one or more times to direct energy toward the one or more objects or materials.

7. The method of claim 1, wherein the tube and the expandable device are delivered to the body lumen via an incision.

8. The method of claim 1, further comprising depositing the one or more objects or materials into a mesh basket positioned proximal to the lumen of the expandable device.

9. The method of claim 8, wherein depositing the one or more objects or materials into the mesh basket includes delivering fluid through the lumen of the tube and into the expandable device.

10. The method of claim 1, wherein the lumen is a biliary duct, and wherein the one or more objects or materials include one or more biliary stones.

11. A method for removing one or more biliary stones from a bile duct, the method comprising:

making an incision in a subject adjacent to the bile duct;

delivering a tube and an expandable device, via the incision, to the bile duct to a position proximal to the one or more biliary stones, wherein the expandable device is positioned with a lumen of the tube, and wherein the expandable device includes a lumen extending from a distal portion to a proximal portion;

delivering a scope through the lumen of the tube and through the lumen of the expandable device, wherein distally advancing the expandable device includes (1) abutting a distal end of the scope with one or more radially inward extensions on an inner surface of the expandable device, and (2) distally advancing the scope to distally advance the expandable device;

proximally retracting the tube such that the expandable device remains in the position proximal to the one or more biliary stones;

distally advancing the expandable device such that the distal portion of the expandable device at least partially surrounds the one or more biliary stones;

at least partially closing a distal end of the expandable device; and moving the expandable device proximally to remove the expandable device and the one or more biliary stones from the bile duct.

12. The method of claim 11, further comprising, before distally advancing the expandable device, expanding the distal portion of the expandable device and dilating a portion of the bile duct by expanding a balloon positioned within a distal portion of the lumen of the expandable device.

13. The method of claim 11, wherein at least partially closing the distal end of the expandable device includes proximally retracting one or more pull lines coupled to the distal end of the expandable device, and wherein proximally retracting the one or more pull lines causes the distal end of the expandable device to taper radially inward to at least partially close the distal end of the expandable device.

14. The method of claim 11, further comprising;

after at least partially closing the distal end of the expandable device and before moving the expandable device proximally, delivering an energy delivery device through the lumen of the tube and the lumen of the expandable device; and activating the energy delivery device one or more times to direct energy toward the one or more biliary stones to fragment or break up the one or more biliary stones.

15. The method of claim 14, further comprising depositing the one or more fragmented or broken up biliary stones into a mesh basket positioned proximal to the lumen of the expandable device.

16. A method for removing one or more biliary stones from a bile duct, the method comprising:

delivering a tube and an expandable device to the bile duct to a position proximal to the one or more biliary stones, wherein the expandable device is positioned with a lumen of the tube, and wherein the expandable device includes a lumen extending from a distal portion to a proximal portion;

delivering a scope through the lumen of the tube and through the lumen of the expandable device, abutting a distal end of the scope with one or more radially inward extensions on an inner surface of the expandable device to distally advance the expandable device;

proximally retracting the tube such that the expandable device remains in the position proximal to the one or more biliary stones;

distally advancing the expandable device such that the distal portion of the expandable device at least partially surrounds the one or more biliary stones;

at least partially closing a distal end of the expandable device;

delivering an energy delivery device through the lumen of the tube and the lumen of the expandable device;

activating the energy delivery device one or more times to direct energy toward the one or more biliary stones to fragment or break up the one or more biliary stones; and moving the expandable device proximally to remove the expandable device and the one or more biliary stones from the bile duct.

17. The method of claim 16, further comprising depositing one or more fragmented or broken up biliary stones into a mesh basket positioned proximal to the lumen of the expandable device.

18. The method of claim 16, wherein at least partially closing the distal end of the expandable device includes proximally retracting one or more pull lines coupled to the distal end of the expandable device.

19. The method of claim 18, wherein proximally retracting the one or more pull lines causes the distal end of the expandable device to taper radially inward to at least partially close the distal end of the expandable device.

20. The method of claim 16, further comprising, before distally advancing the expandable device, expanding the distal portion of the expandable device and dilating a portion of the bile duct by expanding a balloon positioned within a distal portion of the lumen of the expandable device.

* * * * *